United States Patent [19]
Luscombe et al.

[11] Patent Number: 5,683,418
[45] Date of Patent: Nov. 4, 1997

[54] WEDGE SHAPED SUTURE ANCHOR AND METHOD OF IMPLANTATION

[75] Inventors: Brian H. Luscombe, Warren; Dennis D. Jamiolkowski, Long Valley; Jack S. Pedlick, Butler; Izi Bruker, Flemington; Daniel C. Rosenman, Hazlet, all of N.J.; Raymond Thal, Herndon, Va.

[73] Assignee: Mitek Surgical Products, Inc., Westwood, Mass.

[21] Appl. No.: 235,737

[22] Filed: Apr. 29, 1994

[51] Int. Cl.⁶ .................................................. A61B 17/00
[52] U.S. Cl. ........................ 606/232; 606/73; 606/104
[58] Field of Search .................................. 606/232, 148, 606/151, 116, 117, 73, 72, 86, 104, 60, 63

[56] References Cited

U.S. PATENT DOCUMENTS

| | | | |
|---|---|---|---|
| 4,669,473 | 6/1987 | Richards et al. | 606/232 |
| 4,946,468 | 8/1990 | Li | 606/232 |
| 5,085,661 | 2/1992 | Moss | 606/139 |
| 5,102,421 | 4/1992 | Anspach, Jr. | 606/232 |
| 5,174,087 | 12/1992 | Bruno | 53/430 |
| 5,203,787 | 4/1993 | Noblitt | 606/232 |
| 5,207,679 | 5/1993 | Li | 606/232 |
| 5,258,016 | 11/1993 | DiPoto et al. | 606/232 |
| 5,269,809 | 12/1993 | Hayhurst et al. | 606/232 |
| 5,405,359 | 4/1995 | Pierce | 606/232 |
| 5,423,860 | 6/1995 | Lizardi et al. | 606/232 |
| 5,464,425 | 11/1995 | Skiba | 606/232 |

FOREIGN PATENT DOCUMENTS

| | | |
|---|---|---|
| 0 464 479 | 1/1992 | European Pat. Off. . |
| 0 464 480 | 1/1992 | European Pat. Off. . |
| 0 502 509 | 9/1992 | European Pat. Off. . |
| WO 87/01270 | 3/1987 | WIPO . |
| WO 88/09157 | 12/1988 | WIPO . |
| WO 92/04874 | 4/1992 | WIPO . |
| WO 95/08295 | 3/1995 | WIPO . |

*Primary Examiner*—Jeffrey A. Schmidt
*Attorney, Agent, or Firm*—Joseph F. Shirtz

[57] ABSTRACT

A suture anchor is described which in one form may be easily fabricated from extruded material by angular cuts and bore holes which provide an offset pulling force to the suture. In an alternate and preferred embodiment the suture anchor is injection molded having an annular displaced corner and abutment wall which act to seat the suture anchor firmly within a bore hole. Novel application means are also disclosed which hold the suture anchor on a frangible shaft for insertion and upon completion of the insertion permit fracture of the frangible portion and removal of the instrument.

28 Claims, 16 Drawing Sheets

WEDGE SHAPED SUTURE ANCHOR AND METHOD OF IMPLANTATION

TECHNICAL FIELD

The field of art to which this invention relates is surgical implements and more specifically suture anchors for anchoring suture material to bone.

BACKGROUND ART

As the treatment of injuries to joints and soft tissue has progressed in the orthopaedic medical arts, there has been a need for medical devices which can be used to attach tendons, ligaments and other soft tissue to bone. When surgically repairing an injured joint, for example, it is often preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopaedic procedure for reattaching soft tissue to bone is performed by initially drilling holes or tunnels at predetermined locations through a bone in the vicinity of a joint. Then, the surgeon approximates soft tissue to the surface of the bone using sutures threaded through these holes or tunnels. This method, although effective, is a time consuming procedure resulting in the generation of numerous bone tunnels. A known complication of drilling tunnels across bone is that nerves and other soft tissue structures may be injured by the drill bit or orthopaedic pin as it exits the far side of the bone. Also, it is anatomically very difficult to reach and/or secure a suture/wire that has been passed through a tunnel. When securing the suture or wire on the far side of the bone, nerves and soft tissues can become entrapped and damaged.

In order to overcome some of the problems associated with the use of the conventional bone tunnel procedures, suture anchors have been developed and are frequently used to attach soft tissue to bone. A suture anchor is an orthopaedic, medical device which is typically implanted into a cavity drilled into a bone. Although less frequently, these devices have also been referred to as bone anchors. The cavity is typically referred to as a bore hole and usually does not extend through the bone. This type of bore hole is typically referred to as a "blind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure due to abrasion on bone. Suture anchors may be used in the Bankart shoulder reconstruction for repairing the glenohumeral ligament and may also be used in surgical procedures such as rotator cuff repair and hip replacement. Also, such anchors may be used in repair of tendon tears by direct attachment of bone to bone.

Suture anchors typically have at least one suture attached. This may be by means of a hole or opening for receiving the suture(s). At least one end and typically both ends of the suture strand extend out from the bore hole and are used to attach soft tissue. The suture anchors presently described in the art may be made of absorbable materials which absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. In addition, the use of absorbable suture anchors may reduce the likelihood of damage to local joints caused by anchor migration.

Although suture anchors for attaching soft tissue to bone are available for use by the orthopaedic surgeon, there is a constant need in this art for novel suture anchors having improved performance characteristics.

SUMMARY OF THE INVENTION

The device of the present invention calls for an implantable apparatus for wedging within an opening formed within a bone. The apparatus comprises a body which defines a perimeter and said perimeter defining at least one biting edge. A hole is defined by the body through which a suture is received for attachment through the device to the bone. The hole defined by the body may be nearer to one side of the perimeter in order to provide an imbalance of force to increase rotation of the device during the implantation procedure. The body in cross-section may have a perimeter which is substantially in the shape of a triangle, trapezoid or parallelogram. In this way the body may have two sides which diverge in a direction away from said hole, such that the rotation causes an edge formed by one of such sides to bite into the soft cancellous layer of the bone. In order to better distribute the forces acting on the device, the sides may be rounded so that the rounded edge will match with the size of the bore hole provided in the bone. In this way, maximum contact of the edge with the side of the hole in the bone is provided.

The edge may be formed by the intersection of planar or rounded sides or a combination of planar and rounded sides in order to optimize the biting action of the edge. The edge may also be provided with a single engaging tooth or a plurality of engaging teeth in order to improve the holding power, biting and/or placement of the device. The device may be triangular in shape and thus formed by three mutually adjacent sides.

The apparatus may further include a thin longitudinal stem portion which extends from the body. This stem portion is preferably detachable from the body and may be integral and formed with the body out of the same material and provided with a frangible portion or may be formed separately and fitted to the body.

The body may be made of any medical grade material and the stem may be made of a different medical grade material. The body and stem may be joined by a frangible portion which could be formed, for example, by two intersecting web portions in order to provide stability to the device during insertion while still providing the weakness necessary for fracture of the area.

The stem may be provided with a protrusion which mates with an implantation device in order to position the stem within the implantation device at an optimum position.

The body may be made of a bioabsorbable material, a biocompatible metal, or a medical grade polymer for example. The body may be of a medical grade metal material and the stem made of a bioabsorbable polymer such that after fraction the anchor stays implanted but the stem portion remaining after fracture is absorbed by the body.

The invention includes a method of implanting a device for holding material in the bone which comprises accessing the bone and forming an opening therein for receipt of the device. The device is then gripped by a stem which extends from the device and is inserted into the opening by gripping such a stem. The stem is then detached from the device and the device is rotated in order to wedge within the opening formed in the bone.

The separation of the stem from the device may include either breaking a portion of the stem or device in order to separate the stem and device or separating the stem via a snap fit, interference fit, or other attachment mechanism.

The insertion device may include a stabilizing portion to prevent excessive premature rotation of the device and thus prevent premature fracture of any frangible portion of the stem. This however is not necessary in the method where the device is attached to the stem through an interference or frictional fit and the stem is merely removed from an opening in the device during the method of implantation.

BRIEF DESCRIPTION OF THE DRAWINGS

The invention will now be described with reference to the accompanying drawings wherein.

DESCRIPTION OF THE PREFERRED EMBODIMENTS

Figure 1:
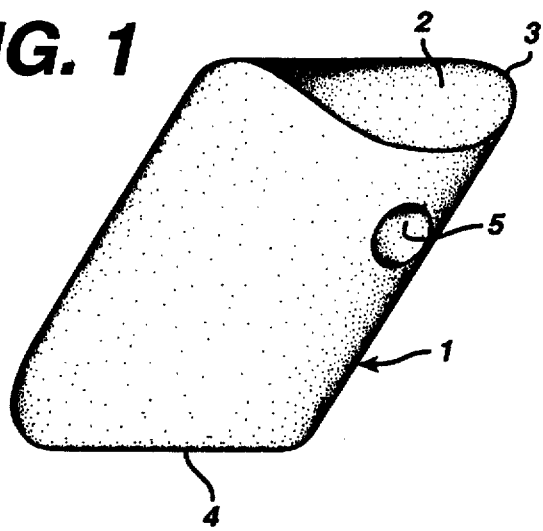
FIG. 1 is a perspective view of a first embodiment of a suture anchor according to the invention.
Figure 2:
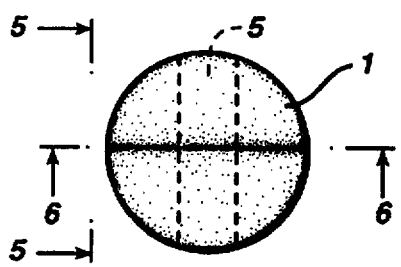
FIG. 2 is an end view of the suture anchor of FIG. 1.
Figure 3:
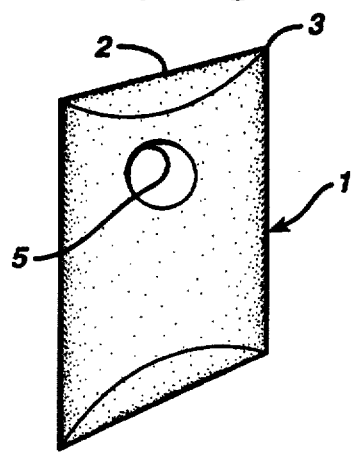
FIG. 3 is a front view of the suture anchor of FIG. 2.
Figure 4:
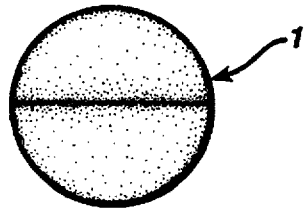
FIG. 4 is an end view of the suture anchor of FIG. 3.
Figure 5:
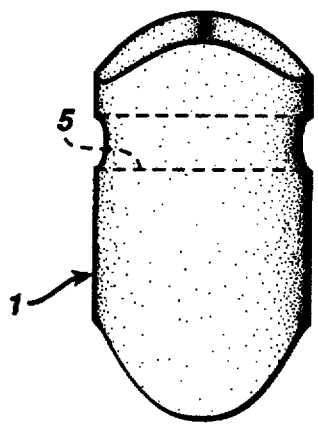
FIG. 5 is a side view of the suture anchor of FIG. 1.
Figure 6:
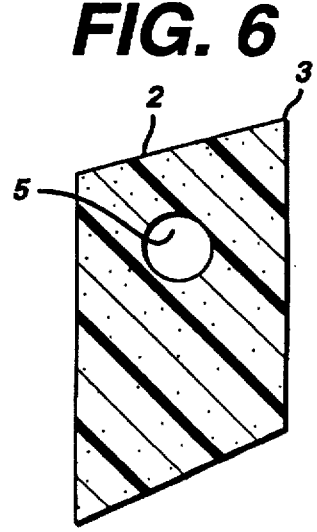
FIG. 6 is a cross-sectional view taken along line 6—6 of FIG. 2.

A first aspect of a suture anchor according to the present invention is a unitized suture anchor, particularly as shown in FIG. 1. The first embodiment of the invention will now be described with reference to the Figures. The suture anchor 1 has a first abutment end 2 and a second abutment end 3. The suture anchor has a substantially cylindrical cross-section as shown in FIG. 2 and the cylindrical longitudinal surface forms with the abutment end 2 a corner 4. The diameter of the suture anchor is sized smaller than the bore hole or opening in the bone receiving the suture anchor. This permits passage of the suture end(s) out of the opening. A suture opening 5 is defined by the body of the suture anchor 1. In an alternative embodiment shown in FIG. 3 the first abutment end 2 and second abutment end 3 are slightly tapered to a point or edge. This is due to the extruding process of formation as will be described below. The suture opening 5 is formed transverse to the longitudinal direction of the suture anchor 1. Also the suture opening 5 is offset from the center of the suture anchor 1 such that an imbalance is formed in the rotation of the device on implantation as described below.

Figure 7:
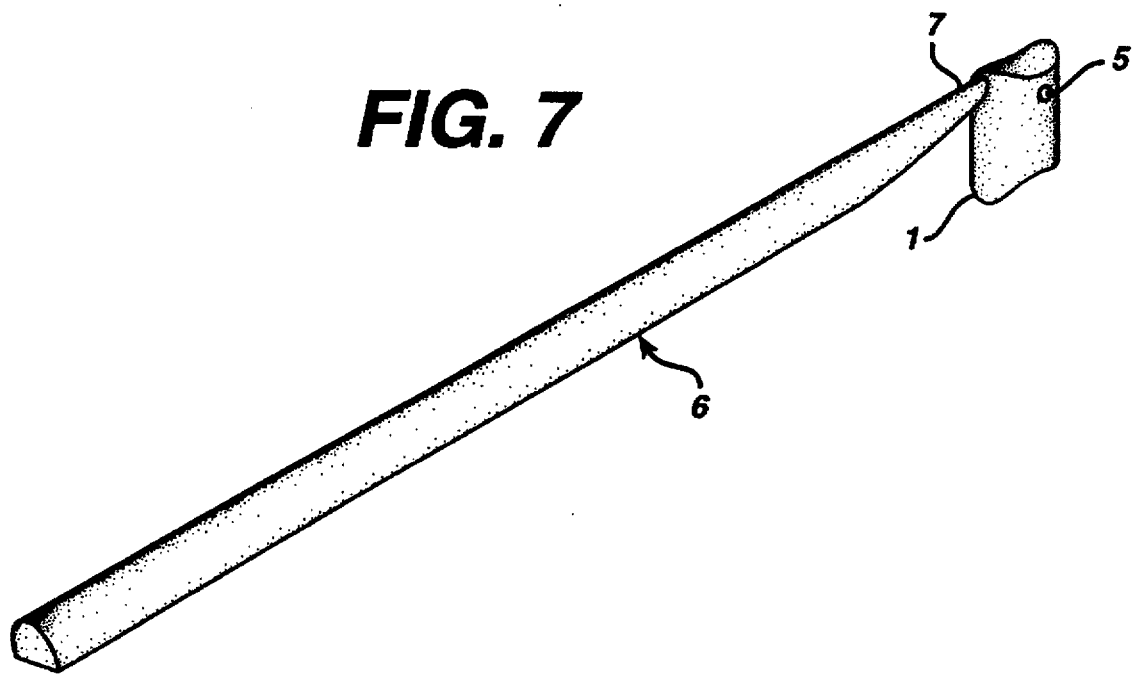
FIG. 7 is a perspective view of the suture anchor and implantation portion of the first embodiment.

The suture anchor may be formed either by extrusion or by injection molding. When injection molding the suture anchor the implantation structure of FIG. 7 is preferred. In that Figure it is seen that a shaft 6 is formed attached to one end of the suture anchor 1. A thinned portion forms a frangible portion 7 which will operate to separate the suture anchor 1 from the shaft 6 upon implantation.

Figure 8:
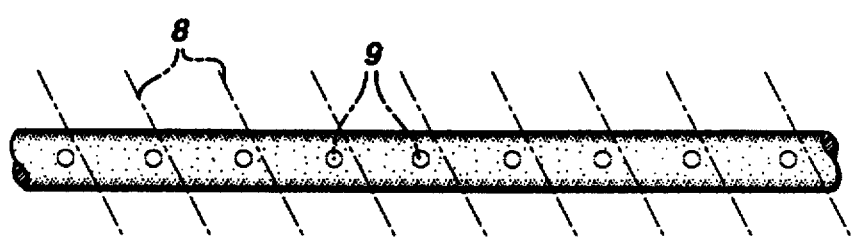
FIG. 8 is a top view of a suture anchor extruded rod blank.

Alternatively, if an extrusion process is used a rod of material is extruded as shown in FIG. 8. Diagonal cuts along cut lines 8 are made after boring openings 9 in the rod at predetermined intervals. Thus, each of the suture anchors is formed by the cut severing the suture body from the suture body of the adjacent anchor.

Figure 9:
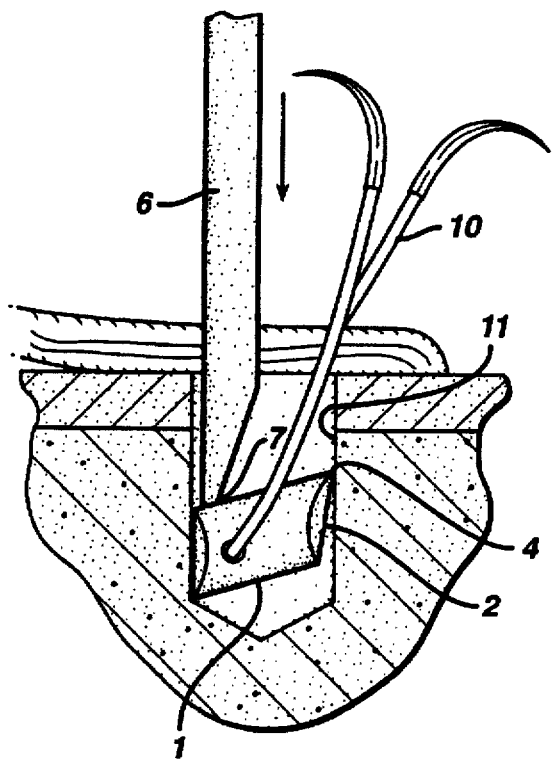
FIG. 9 is a view of the implantation procedure of the present invention.
Figure 10:
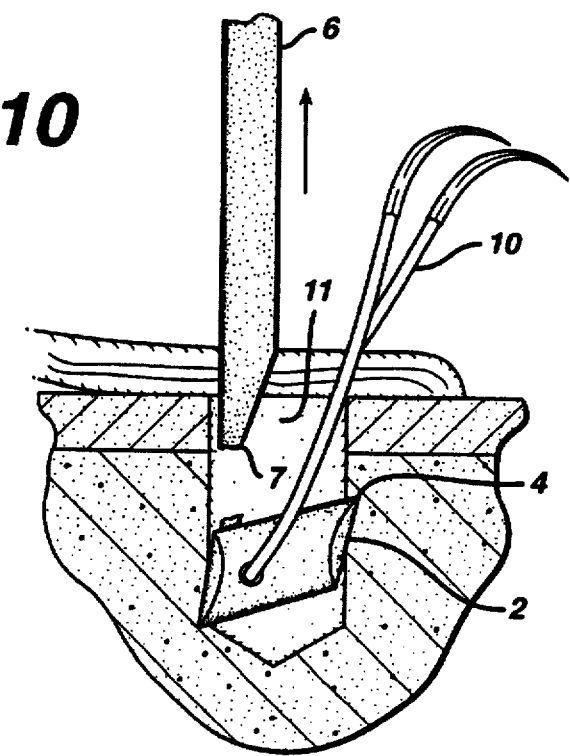
FIG. 10 is a view of the implantation procedure upon removal of the implantation device.

Now an implantation procedure will be described. With reference to FIG. 9 the suture anchor 1 has a suture 10 passed through the opening 5. An appropriate implantation site is created by, for example, boring a hole of predetermined dimension in the bone material slightly larger than the diameter of the suture anchor. The hole may have a diameter of 5 mm for a suture anchor of 3 mm size and is drilled through the outer cortex of the bone into the inner cancellous layer. Upon insertion the suture anchor is placed within the bore hole by the downward motion as shown in FIG. 9. An upward tug on the shaft portion 6 causes a series of events to occur. Initially corner 4 digs into the softer cancellous layer of the bone and second abutment end 3 rotates into engagement with the opposite of the wall. Thus, the anchor is wedged within the opening of the bore hole 11. The shaft 6 separates from the suture anchor 1 by the breaking of frangible portion 7. This leaves the suture anchor 1 implanted within the bone while the shaft 6 is removed. This securely implants the anchor within the bone material permitting attachment of soft tissue or other materials through the use of suture 10.

Figure 11:
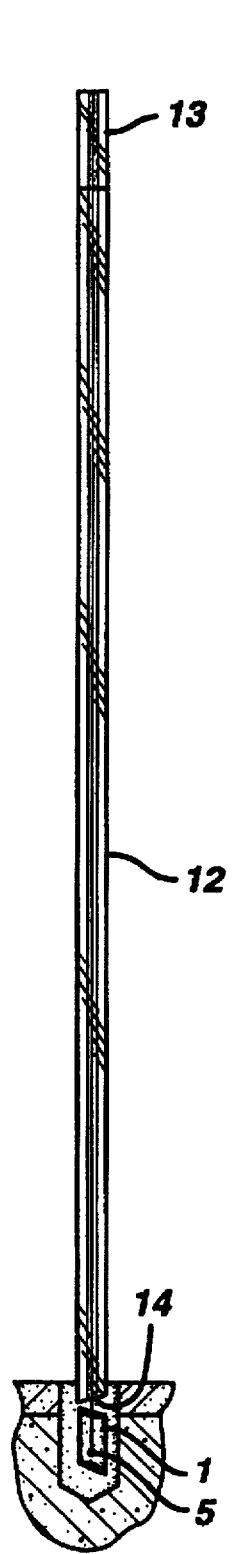
FIGS. 11 and 12 show an alternative implantation procedure for the device of FIG. 1.
Figure 12:
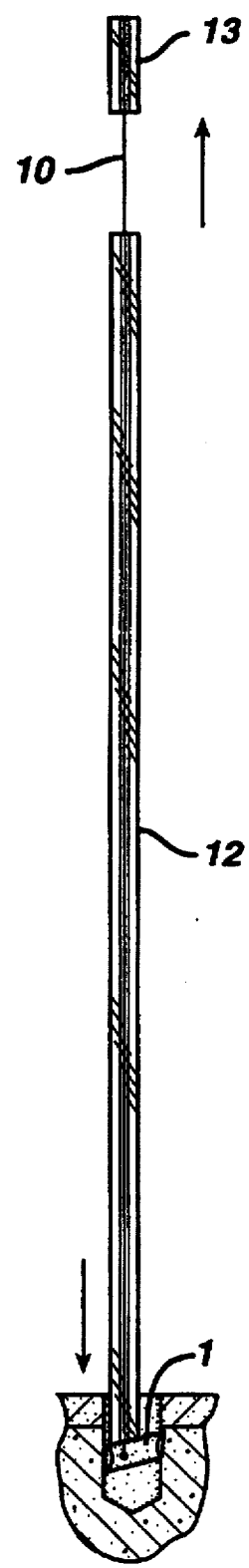
Figure 13:
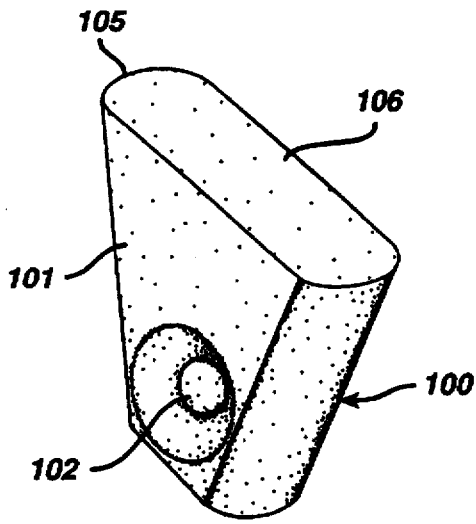
FIG. 13 is a perspective view of an alternate embodiment of the suture anchor of the present invention.

An alternative arrangement for implantation is shown in FIGS. 11 and 12. This arrangement may have the suture already in place such that a preloaded anchor and apparatus is provided. The apparatus includes a tube 12 which may be formed to receive therein the suture anchor 1. The suture 10 is preloaded through the opening 5 defined in the suture anchor and passed up through the tubular portion to a pull tab 13. An appropriate bore hole 11 is prepared in the bone and the suture anchor and tube are inserted therein. The suture anchor is permitted to drop out of the tubular portion and becomes slightly dislocated with respect to the tube. End 14 of the tube is cut at a slight angle in order to promote the rotation of the suture anchor in a particular direction. For example, as shown in FIGS. 11 and 12, the suture anchor is promoted to rotate in a clockwise direction by the longer portion of the tube being on the left side of the figure, that is the longer side of the suture anchor. Once the suture anchor has dropped out of the tube 12, the pull tab 13 is used to snug up the suture anchor within the opening. By pulling upward on the pull tab, the biasing force of the offset hole acting through the pulling force of the suture firmly anchors the suture within the opening. At this point, the pull tab may be removed and the suture slid from within the tubular portion 12.

An embodiment will now be described with reference to FIGS. 13–26. The suture anchor 100 has a body 101 formed in a substantially truncated wedge shape. The body 101 defines a suture opening 102 which is rounded at its openings in order to avoid the likelihood of abrasion to the suture. An abutment wall 103 may be straight but in the preferred embodiment is provided with a radiused surface which extends in an oblique direction of the anchor. This radius is set to match the radius of the bore hole into which the anchor is intended to be inserted. For example a 4 mm diameter hole would be drilled to receive an anchor with a 4 mm radius to abutment wall 103. A plow wall 104 forms an edge 105 at its intersection with top 106 of the device. The plow wall 104 is also radiused in order to maximize contact between edge 105 and the wall of the bore hole to improve the action of the corner 105 as both a plow and a frictional engagement mechanism for the anchor.

Figure 14A:
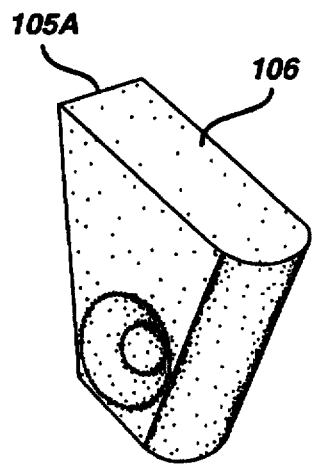
FIG. 14 a–d show various embodiments of the plow edge of the device of the present invention.
Figure 14B:
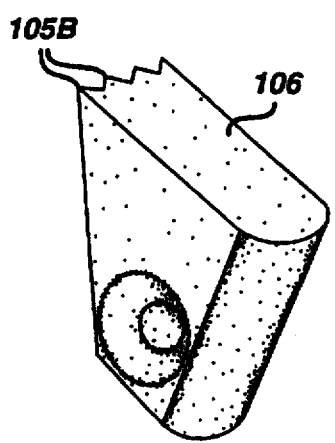
Figure 14C:
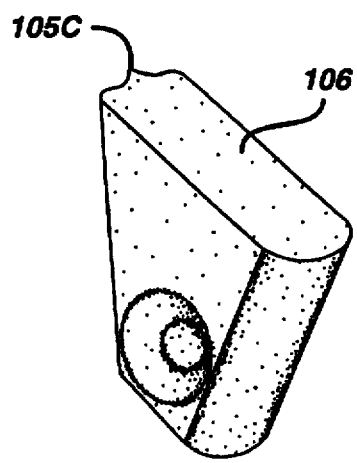
Figure 14D:
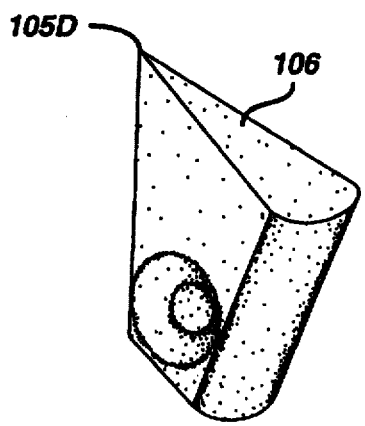
Figure 15:
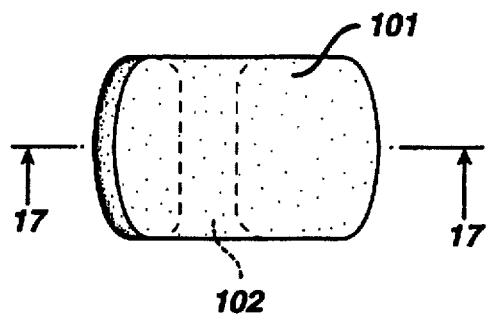
FIG. 15 is a top view of the suture anchor of FIG. 14.
Figure 16:
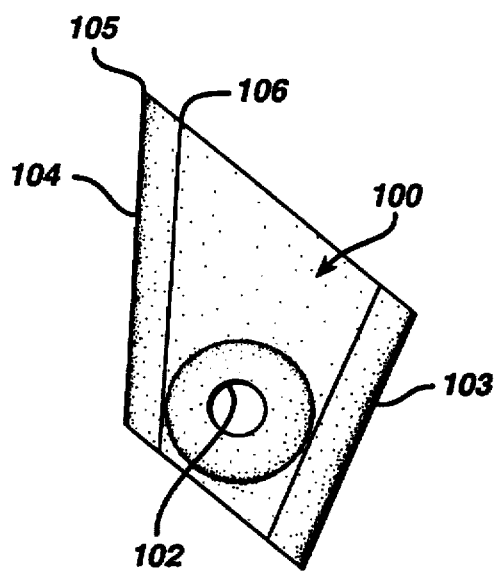
FIG. 16 is a front view of the suture anchor of FIG. 14.
Figure 17:
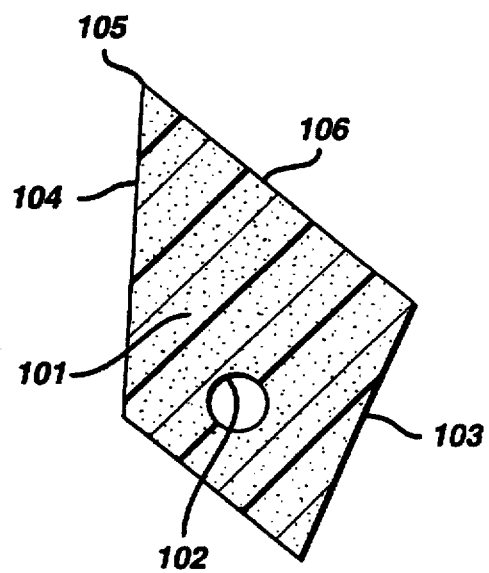
FIG. 17 is a cross-sectional view taken along line 17—17 of FIG. 15.

The corner or edge 105 may be formed in a plurality of manners. For example, the edge 105 (FIG. 14A may be straight and squared off at the junction between walls 106 and 104, or the edge 105 may be formed with a plurality of teeth 105B to provide additional digging force. Also, the embodiment of FIG. 14B may be modified as shown in FIG. 14C to provide but a single tooth or point which would initiate the digging effect of the edge 105C to introduce the remainder of the edge into the soft cancellous layer. Finally, an additional alternative embodiment is shown in FIG. 14D wherein the edge 105 is actually a point 105D and the plow wall 104 is actually an edge such that the body of the anchor has a substantially conical or cylindrical cross section.

Figure 18:
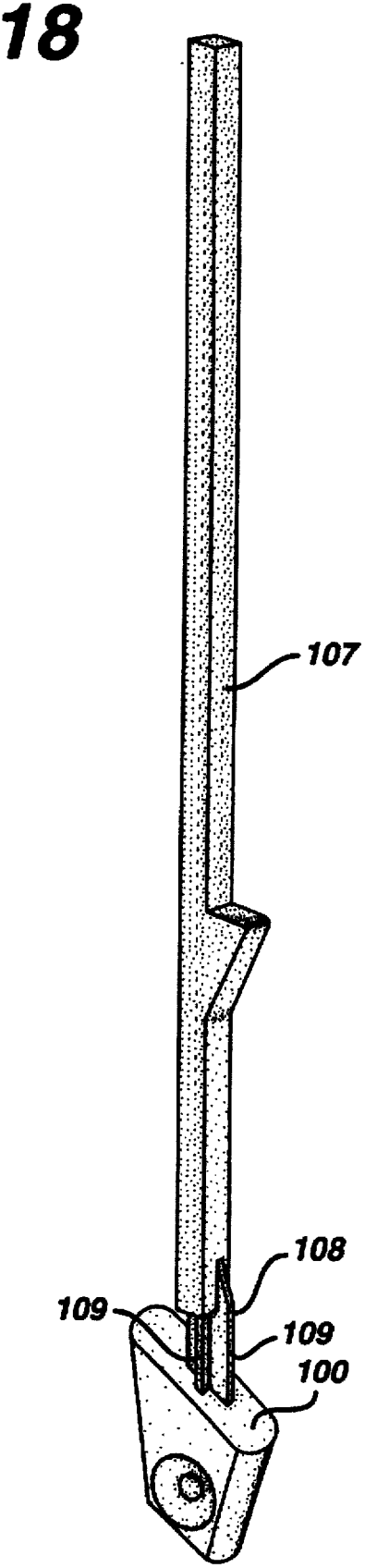
FIG. 18 is a perspective view of the suture anchor of FIG. 14 with a unitized implantation device.

FIG. 18 shows a shaft 107 that extends from the top of the suture anchor prior to insertion of the device into the bore hole. The shaft 107 has formed therein frangible portion 108 in this case formed by a pair of intersecting webs 109. This structure is preferred in the unitized injection molded form of the device as it provides stability between the shaft and suture anchor by maximizing the area moment of inertia of the cross-section while still maintaining a weakness to separation permitting fracture at the frangible portion by minimizing the cross-sectional area.

A stop 110 is provided in order to locate the device in an insertion apparatus prior to implantation. The entire device is injection molded out of a polymer material. The angles of junction for the abutment wall 103 and the top 106 range from about 60° to about 140° and is preferably about 105°. The angle for corner 105 at the juncture of plow wall 104 and top 106 ranges from about 20° to about 90° and preferably about 55°.

The anchors of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends or other combinations thereof and equivalent thereof. Of particular utility are the polylactides, especially poly[L(-)lactide], and the lactide-rich lactide/glycolide copolymers, especially 95/5 poly[L(-)lactide-co-glycolide].

Examples of non-absorbable materials from which the suture anchors of the present invention may be made include metallic biocompatible materials including stainless steel, Nitinol, titanium, Vitalium and equivalents thereof, polymeric materials such as non-absorbable polyesters, polyamides, polyolefins, polyurethanes, and polyacetals and equivalents thereof.

The bonding of the anchors of the present invention to bone may be advantageously increased by promoting bone growth. This can be accomplished by having a microporous surface into which the bone can rapidly grow to aid fixation. This may be particularly advantageous in the case of a metallic anchor, especially a titanium or titanium alloy anchor, but may also provide benefit in the case of polymeric anchors of the present invention, especially those made of absorbable materials. Other methods include the coating of the anchor's surface with a substance to promote adhesion to the bone. Such coatings include the hydroxyapatite-containing-glass coatings described by Ishikawa, et al., in the article "Effect of Hydroxyapatite Containing Glass Coating on the Bonding between Bone and Titanium Implants" appearing in Clinical Materials, Volume 14, 1993, pages 277–285.

It is further noted that the anchors of the present invention can be made to contain growth factors, especially bone growth factors, that can advantageously increase the effectiveness of the anchors, especially in the area of fixation. This may be accomplished in a number of ways, including via coatings or, in the case of absorbable materials by incorporating the growth factors within the device and allowing them to diffuse out.

The suture anchor devices of the present invention, when made from an absorbable material, are preferably manufactured by molding using conventional injection molding equipment and conventional injection molding processes. A typical molding process includes the steps of (1) injecting a suitable polymer melt into an appropriately designed mold or cavity at process conditions conventionally employed for such polymer systems, (2) releasing from the mold, after the melt cools in the mold, polymer shaped in the proper configuration to meet the design criteria of the device. Additionally the anchor molded from the absorbable polymeric material, may be advantageously subjected to an annealing process to increase its mechanical or biological performance. Thermal annealing can also be used to increase the dimensional stability of molded parts by increasing the crystallinity levels in the parts. One or more surgical sutures, or one or more sutures with surgical needles attached, may be used in combination with the suture anchor and may be assembled prior to sterilization. The device can then be sterilized using conventional methods to render the anchor suitable for surgical applications.

Figure 19:
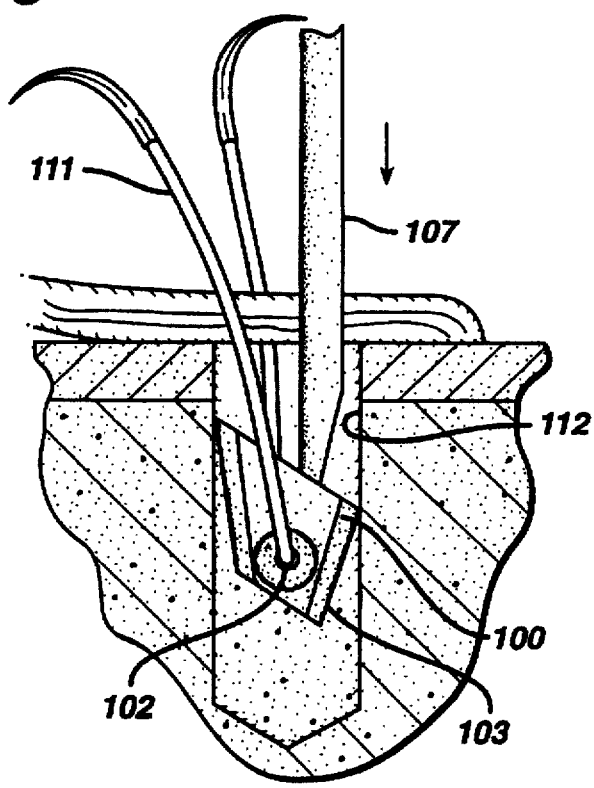
FIGS. 19 through 22 show the implantation procedure of the suture anchor.
Figure 20:
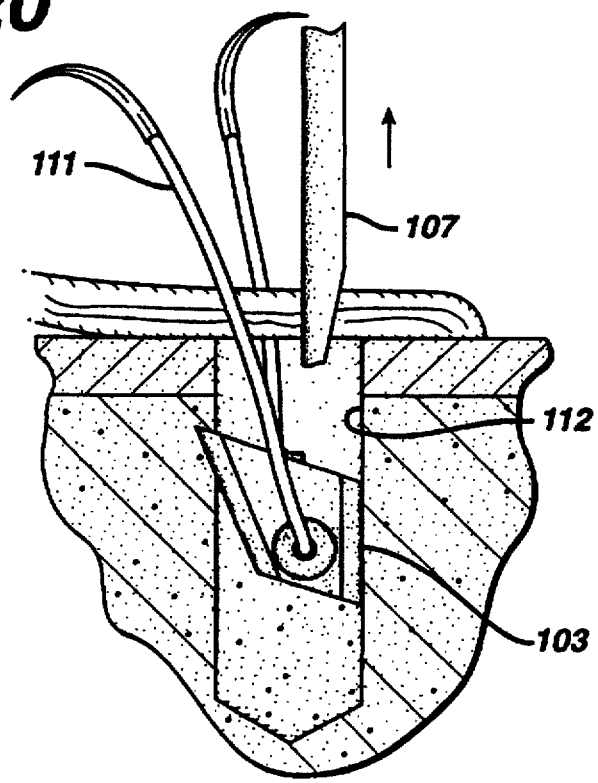
Figure 21:
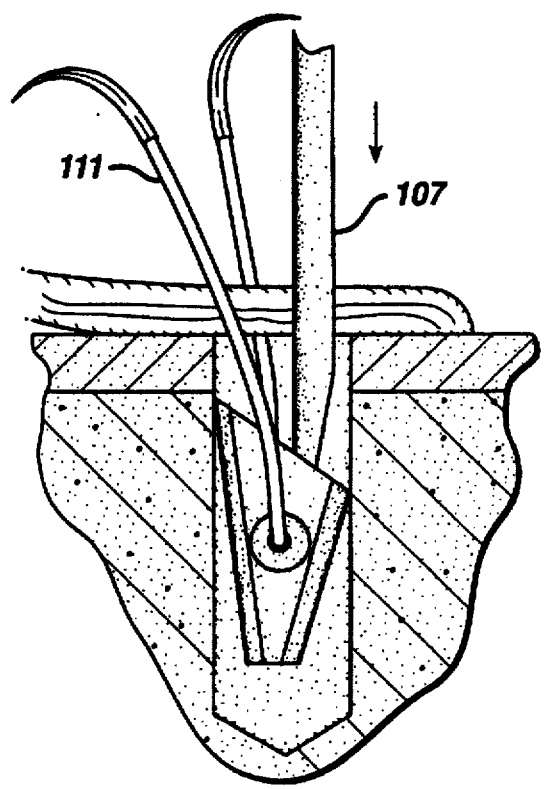
Figure 22:
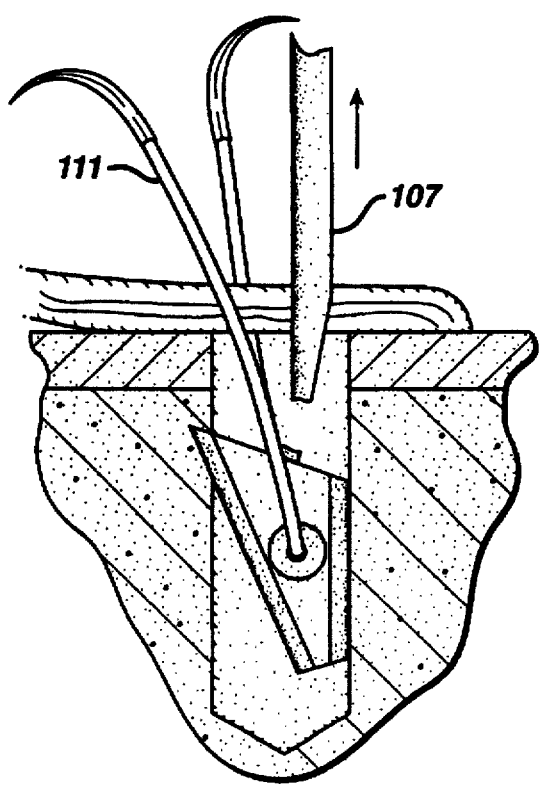

Referring now to FIGS. 19 and 20 the implantation procedure is displayed. Referring to FIG. 19 the suture anchor 100 with shaft 107 attached thereto is inserted into a bore hole after threading of a suture 111 through suture opening 102. The device is inserted gently into the bore hole until the suture anchor bottoms out in the hole as shown in FIG. 19. It is not desired to bottom out the suture anchor. After full insertion or bottoming out the applier (of the type in FIGS. 28 and 29), the shaft is drawn upward forcing the edge 105 to dig into the softer cancellous layer of the bone. The edge digging in on withdrawal of the shaft creates a rotation of the body of the suture anchor which, in combination with the withdrawal tension, breaks the frangible portion 108 and permits removal of the shaft 107 after separation. The suture anchor itself rotates fully until abutment wall 103 is engaged firmly against the surface of the hole 112 formed in the bone. In this case the corner 105 is formed at about a 40° angle between the top 106 and the plow wall 104. Further, abutment wall 103 and top 106 meet to form an angle of about 105°. The top has a length of about 4.6 millimeters and the abutment wall has a length of about 3.2 millimeters and plow wall 104 has a length of about 3.6 millimeters. These dimensions while specific to this embodiment are proportional in all sizes of the suture anchor being used. That is, a larger suture anchor is made by merely proportionally increasing the dimensions while maintaining the angular relationship of the sides, walls and top in the same configuration. As can be seen in FIGS. 21 and 22, this embodiment can be supplied in a longer version which will require a deeper hole.

Figure 23:
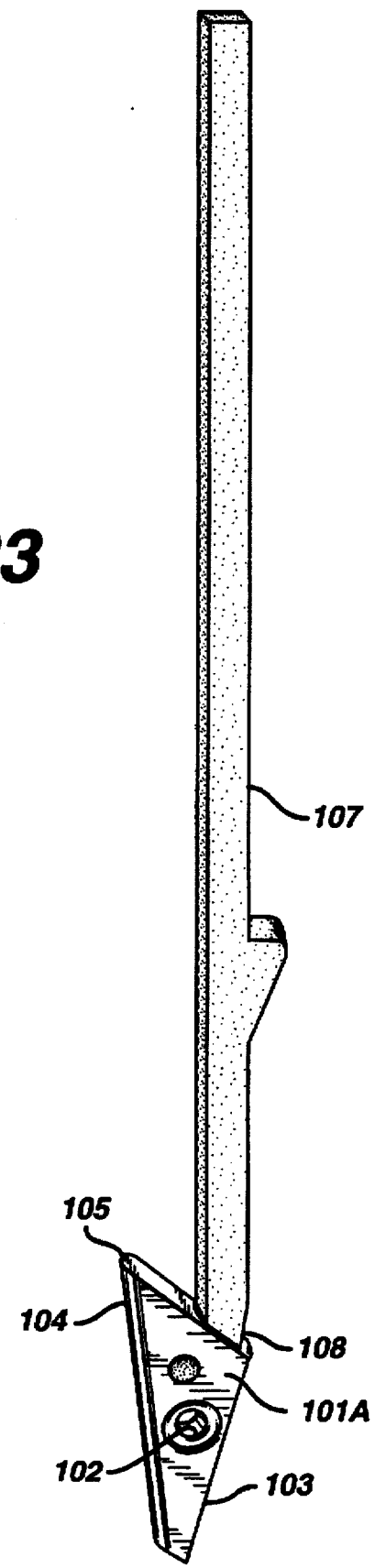
FIG. 23 is a perspective view of a metal suture anchor according to the present invention.

An alternative embodiment as shown in FIG. 23 wherein the body 101A is formed of a metal substance such as a titanium alloy. Preferably the alloy is Ti-6Al-4V alloy. The metal body 101A has a similar suture opening 102 defined therein. An abutment wall 103 and plow wall 104 are provided as in the polymer version of the device and the plow wall 104 forms a corner 105 with the top in a similar fashion. The metal version is provided with a polymer shaft 107 having frangible portion 108 as is provided in the previous embodiment. The metal body 101A is inserted into an injection mold and shaft 107 formed by injection molding the shaft into the metal body 101A. Two intersecting openings are formed (FIG. 23A) to provide a volume to be filled with polymer. The remainder of the metal device is substantially similar to the device of the previous description.

The shaft 107 of the metal version of the anchor may be made of any suitable biocompatible material such as medical grade polymers and may be a bioabsorbable material such as poly[L(-)lactide].

Figure 24:
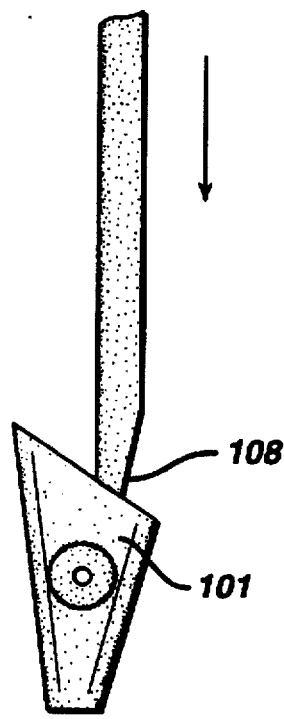
FIG. 24 is a front view of a molded suture anchor according to the present invention.
Figure 25:
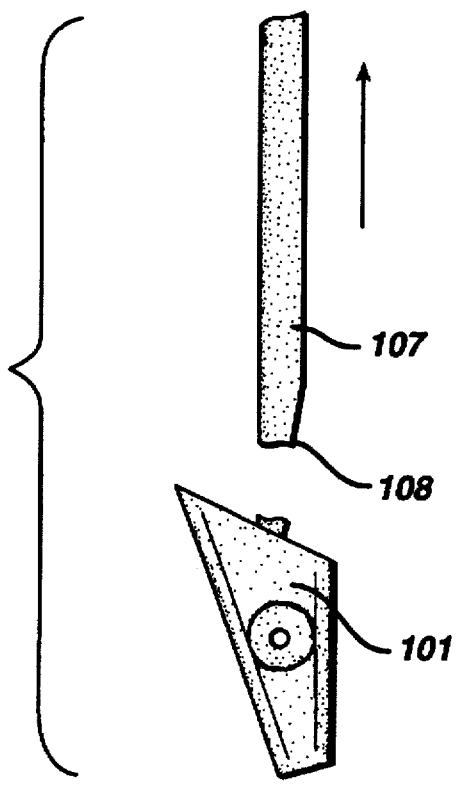
FIG. 25 is a front view of a molded suture anchor according to the present invention after implantation.

FIGS. 24 and 25 show the rotational movement of the body 101 of the suture anchor upon implantation. This rotational movement provides torsional forces to the frangible portion 108 of the shaft 107 to promote the fracture of the shaft at the frangible location.

Figure 26:
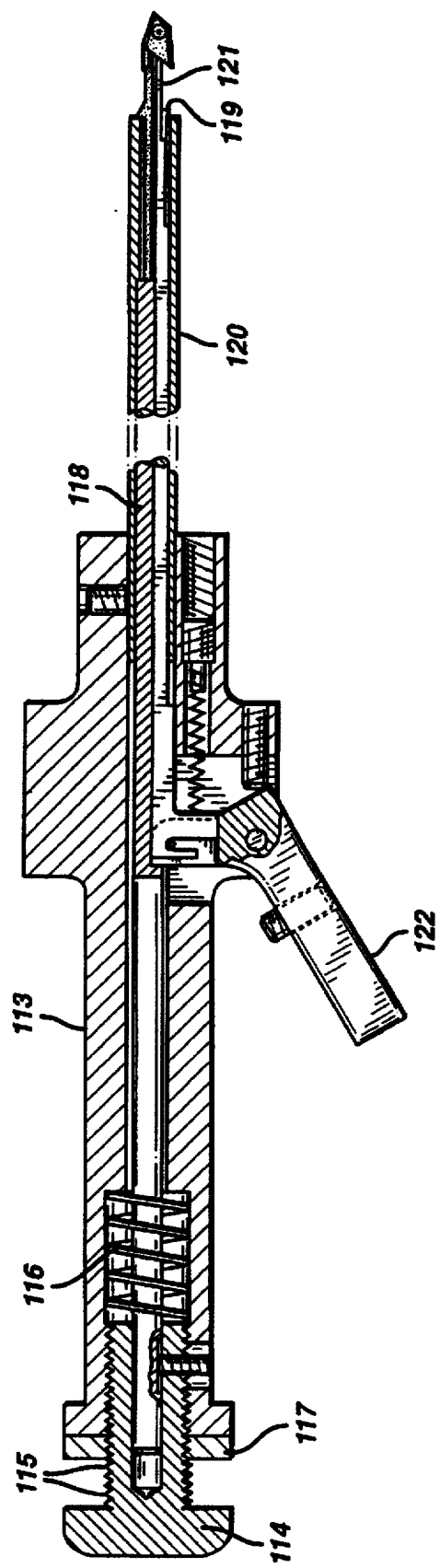
FIG. 26 is an alternative instrument for implanting the suture anchor of the present invention.

A novel insertion mechanism is shown in FIG. 26. The applicator 113 has a screw handle 114 having threads 115 formed thereon. The screw handle is adjusted by rotation against the spring force of spring 116. Once positioned, the screw handle is locked in place using locking ring 117, which is threaded down tightly against the back surface of the applicator 113. A shaft 118 extends from the screw handle 114 along the length of the applicator 113. The shaft has a wedged end 119 which is received substantially within a tubular portion 120 of the applicator. The device may be used in an open procedure. But, tubular portion 120 permits optional insertion of the applicator into a trocar for arthroscopic surgery.

The wedged end 119 is extended from within the tubular portion 120 by the rotation of screw handle 114 to permit extension of the shaft 118 and in particular, the wedge end 119 out of the tubular portion 120. The shaft 107 of the suture anchor is inserted into the tubular portion 120 until the stop 110 seats firmly against the tubular portion 120 of the applicator 113. At this point the screw handle is threaded in the opposite direction in order to draw the wedge end 119 within the tubular portion. The wedging or camming effect of the wedge end 119 firmly grasps the shaft 107 of the suture anchor and holds it within the device.

A finger 121 extends from the end of tubular portion 120 and seats along the top surface of the suture anchor in order to stabilize the body. This prevents premature rotation of the suture anchor and fracture of the frangible portion prior to complete insertion. The finger translates along the longitudinal portion of the tube in response to motion of trigger 122. Upon use the device is inserted into a trocar in order to provide access arthroscopically to the surgical site. The suture anchor is placed into the previously bored bore hole and trigger 122 is manipulated. The manipulation of trigger 122 moves the finger 121 in the longitudinal direction. This forces rotation of the suture anchor body and promotes the fracture of the frangible portion of the shaft while holding the anchor in position. Simultaneously with manipulating the finger 121 the device is withdrawn thus completing the fracture of the frangible portion of the shaft. The previously threaded suture is then used to attach soft tissue according to known surgical procedures.

Figure 27:
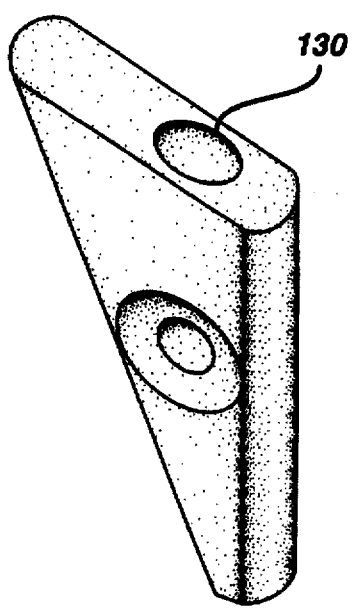
FIG. 27 is a front perspective view of an alternate embodiment of the suture anchor of the present invention.

Referring now to FIG. 27, an alternate and preferred embodiment is shown. The body of the suture anchor is shaped as described above, however a mounting opening 130 is provided at one end of the body of the device. This opening is sized to receive the mounting end 131 of the insertion device shown in FIGS. 28 and 29. The insertion device 132 having mounting end 131 is comprised of an elongated shaft 133. The shaft has two sections, a narrower distal section and a wider proximal section separated by a transitional section 134. The transitional section 134 is conical in shape for reasons which will be described below in connection with the implantation procedure. A handle 135 is provided at the proximal end of the insertion device to facilitate gripping of the device during the implantation procedure.

Figure 28:
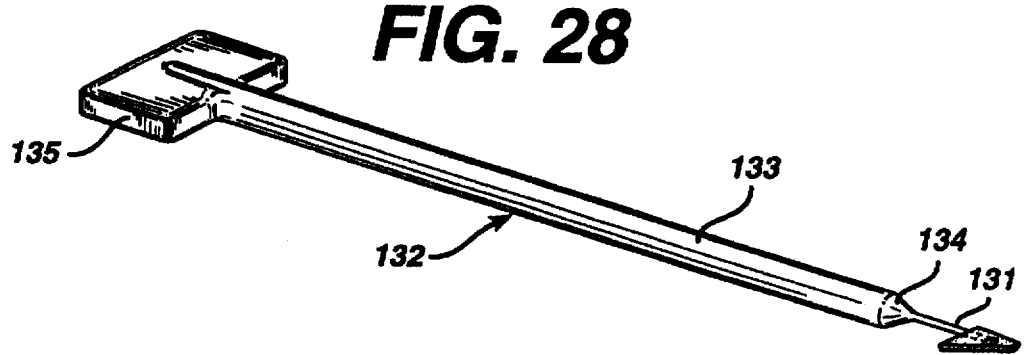
FIG. 28 is a perspective view of an alternate embodiment of the implantation device of the present invention with suture anchor attached.
Figure 29:
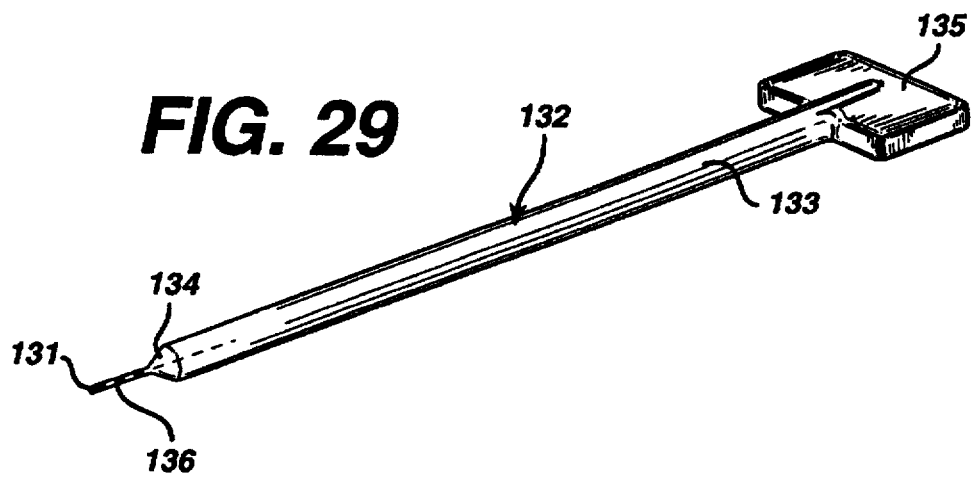
FIG. 29 is a perspective view of the implantation device of FIG. 28.
Figure 30:
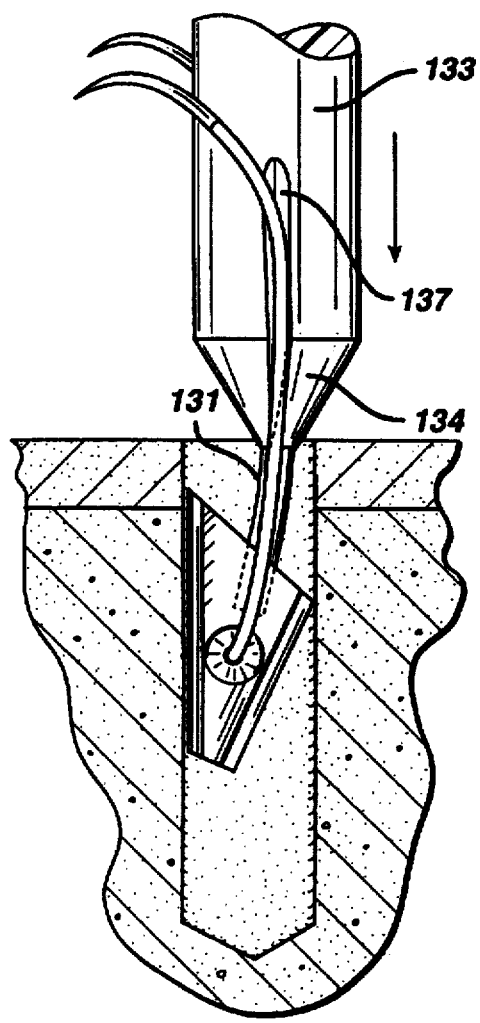
FIG. 30 is a partial cross-sectional view showing implantation of a suture anchor using the device of FIGS. 28 and 29.
Figure 31:
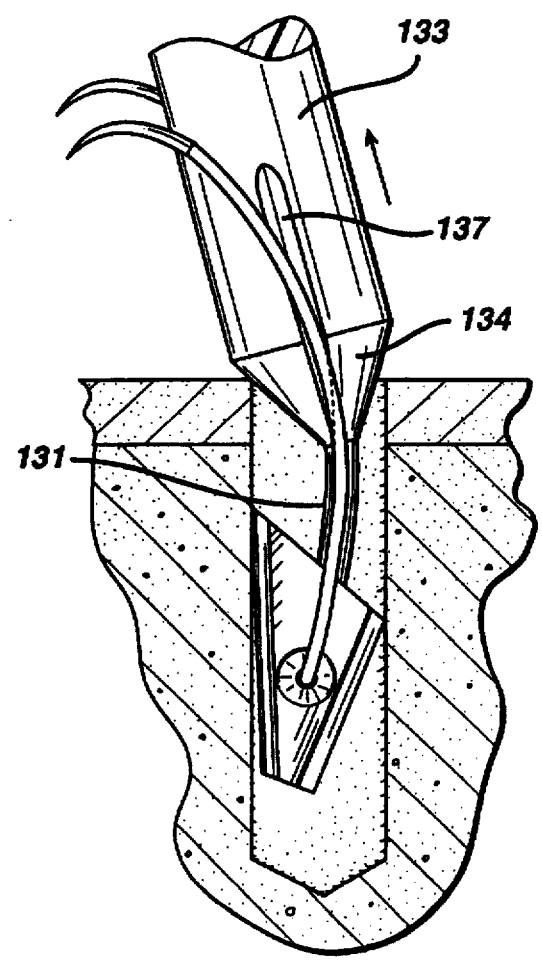
FIG. 31 is a partial cross-sectional view showing implantation of a suture anchor using the device of FIGS. 28 and 29.
Figure 32:
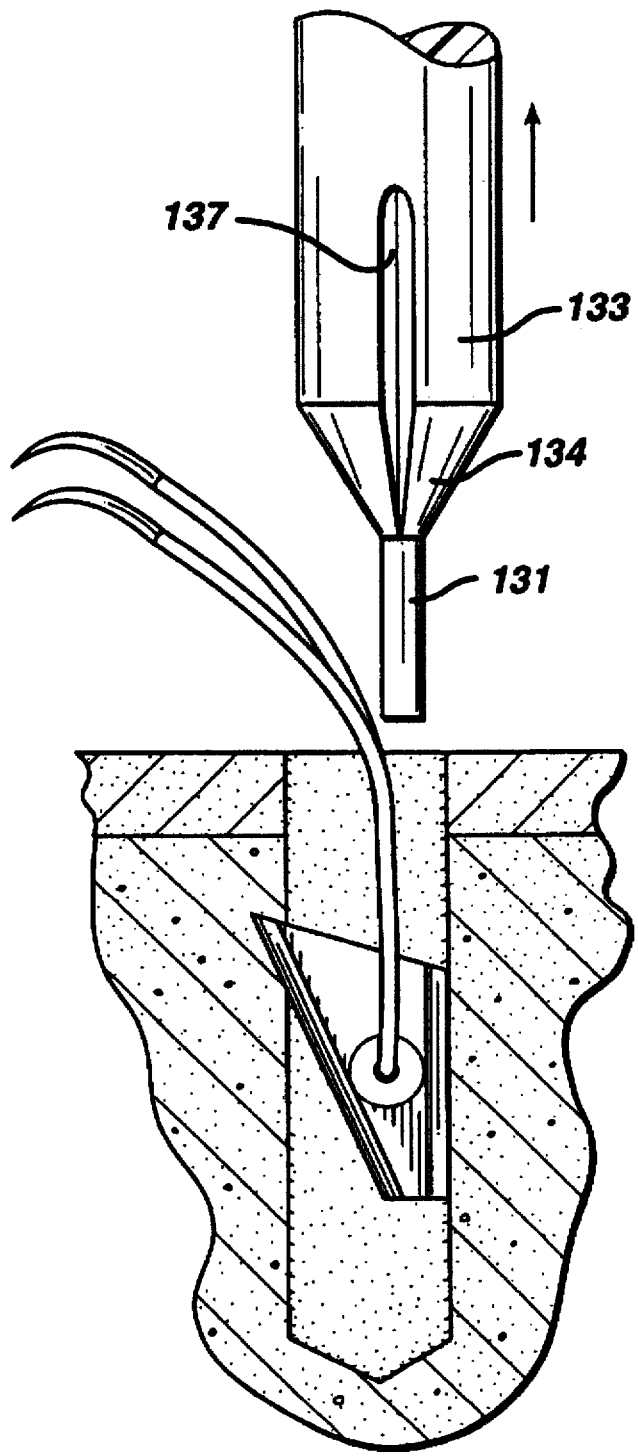
FIG. 32 is a partial cross-sectional view showing implantation of a suture anchor using the device of FIGS. 28 29.

In use, (FIGS. 30 and 31) insertion end 131 is received within mounting opening 130 of the body of the suture anchor as shown in FIGS. 28 and 29. Mounting opening 130 is offset from the center line of the body of the suture anchor for reasons which will become apparent below. During the insertion procedure the suture anchor is inserted into a previously-formed bore hole. The insertion tool travels in a position off axis from the hole in the bone. Once the transition portion 134 reaches the top of the bore hole the transition surface forces the insertion tool towards the axis of the bore hole (i.e., the transition portion causes the tool to center). This causes the distal end of the tool to flex slightly and provides additional torque to the suture anchor assisting the plow edge in digging into the bone. A pair of slots 137 are provided to permit the protected passage of the suture out of the bore. Upon removal of the insertion tool, (FIG. 32) the flex of the tool forces the plow edge of the suture anchor into the soft cancellous portion of the bone and the distal tip of the insertion tool slips out of the mounting opening 130 due to the upward force provided on the insertion tool. This provides an extra impetus to the insertion of the suture anchor and its final implantation and mounting.

In an alternative embodiment the insertion tool may be provided with a distal end 136 of a soft polymer material having therein a stiffening member such as a metal wire or polymer of more rigid material. Thus, a soft and manipulable insertion tool is provided having the resilience at the distal end to provide the insertion forces described above. The softer polymer insertion tool aids in producing a friction fit between the distal tip of the insertion tool and the mounting opening 130. Thus, a more sure grip is provided between the tool and the body of the suture anchor.

In general the mounting opening 130 need not be cylindrical in shape. The mounting opening and distal tip of the insertion tool may be shaped so as to prevent rotation of the suture anchor about the tip.

Figure 33:
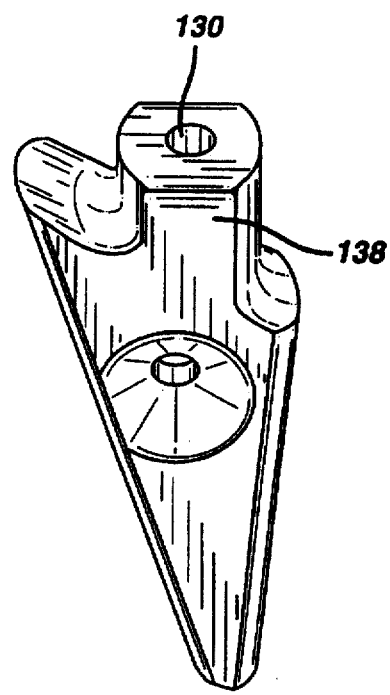
FIG. 33 is an alternate embodiment of the suture anchor of the present invention; and, FIG. 34 is a partial cross-sectional view showing implantation of the suture anchor using the device of FIG. 33.
Figure 34:
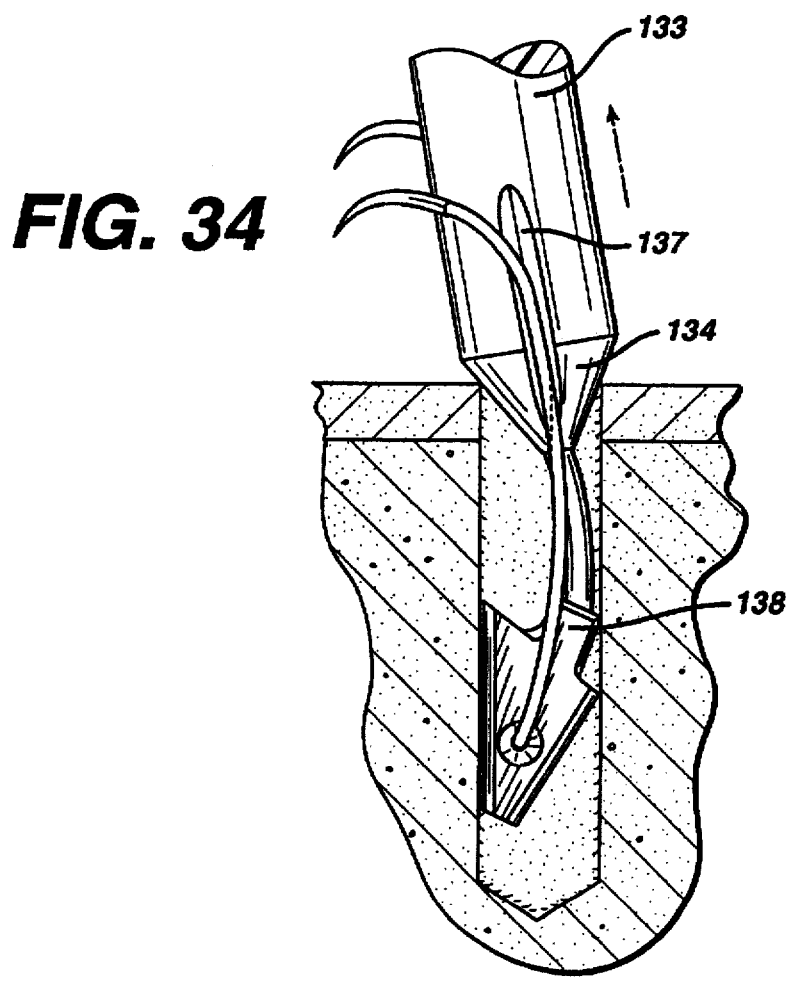

A further embodiment developed for single piece polymer anchors is shown in FIGS. 33 and 34. The anchor has substantially the same shape as the anchors described above, however a protuberance 138 extends from the top surface of the wedge. This protuberance has formed therein the mounting opening 130 which receives the insertion tool described above as shown in FIG. 34. This protuberance provides an area for defining the mounting opening 130 such that the opening is not formed within the body of the wedge, possibly weakening the wedge.

Thus, the invention has been described with reference to the attached drawings. It is easily understood by one of ordinary skill in the art that changes may be made to the embodiments described herein without exceeding the spirit or scope of the attached claims.

We claim:

1. An implantable apparatus for wedging within an opening formed within a bone comprising a body having a longitudinal cross-section defined by a perimeter, said cross-section being a quadrilateral shape and, said perimeter forming at least one biting edge, said body further defining a hole through said body in a direction transverse to said cross-section.

2. The apparatus according to claim 1 wherein said body perimeter is in the shape of a trapezoid.

3. The apparatus according to claim 1 wherein said body perimeter is in the shape of a parallelogram.

4. The apparatus according to claim 1 wherein the perimeter is defined by four sides and two of the sides diverge in a direction away from said hole.

5. The apparatus according to claim 4 wherein said two of the sides have a longitudinal extent and are rounded transverse to said longitudinal extent.

6. The apparatus of claim 5 wherein said two sides are rounded to a radius approximately equal to a radius of the opening formed within the bone.

7. The apparatus according to claim 4 wherein at least one of said sides is substantially planar.

8. The apparatus according to claim 7 wherein at least one of said sides is rounded.

9. The apparatus according to claim 1 wherein said hole is nearer to one side than it is to a noncontiguous second side.

10. The apparatus according to claim 1 wherein said biting edge forms at least one engaging tooth.

11. The apparatus according to claim 10 wherein said biting edge forms a plurality of biting teeth.

12. The apparatus according to claim 1 wherein said hole has received therein a suture.

13. The apparatus according to claim 12 wherein said suture has at least two free ends extending from said body.

14. The apparatus according to claim 1 wherein the apparatus is presented in a sterile condition prior to use.

15. The apparatus according to claim 1 wherein said perimeter is formed of three mutually adjacent sides.

16. The apparatus according to claim 1 further including a thin longitudinal stem portion extending from said body.

17. The apparatus according to claim 16 wherein said stem is integral with and formed of the same material as said body.

18. The apparatus according to claim 16 wherein said body is of a medical grade material and said stem is of a different medical grade material.

19. The apparatus according to claim 16 wherein said stem is connected to said body by a frangible portion.

20. The apparatus according to claim 19 wherein said frangible portion is formed of at least two intersecting web portions forming a cross.

21. The apparatus according to claim 16 further including a protrusion on said stem for positioning of said stem within an implantation apparatus.

22. The apparatus according to claim 16 wherein said body is made of a medical grade metal material and said stem is made of a bioabsorbable polymer.

23. The apparatus according to claim 1 wherein the body material is made of a bioabsorbable material.

24. The apparatus according to claim 1 wherein the body material is of a biocompatible metal.

25. The apparatus according to claim 1 wherein said body is made of a medical grade polymer.

26. The apparatus according to claim 1 wherein an inserter is attached to said body and said inserter has an upper portion and a lower portion and said upper portion is of a diameter larger than a diameter of said lower portion and a transition zone extends between said upper portion and lower portion for positioning said body within an opening during an implantation procedure.

27. The apparatus according to claim 26 wherein said inserter further defines at least one longitudinally extending slot in the upper portion at about the transition zone for passage of a suture to prevent damage during the insertion process.

28. The apparatus according to claim 26 wherein said body is formed of a metal and said inserter is received through friction fit in hole defined in one end of said body.

* * * * *